United States Patent
Apel et al.

(10) Patent No.: US 7,166,548 B2
(45) Date of Patent: Jan. 23, 2007

(54) APATITE GLASS CERAMIC BASED ON SILICEOUS OXYAPATITES

(75) Inventors: Elke Apel, Buchs (CH); Wolfram Höland, Schaan (LI); Christian van't Hoen, Feldkirch (AT); Urs Bolle, Feldkirch (AT); Volker M. Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 25 days.

(21) Appl. No.: 10/973,233

(22) Filed: Oct. 26, 2004

(65) Prior Publication Data
US 2005/0209082 A1    Sep. 22, 2005

(30) Foreign Application Priority Data
Mar. 18, 2004   (DE) .................. 10 2004 013 455

(51) Int. Cl.
C03C 10/04   (2006.01)
(52) U.S. Cl. .................. 501/5; 501/6; 106/35; 65/33.1; 65/334

(58) Field of Classification Search ............ 501/5, 501/6; 65/33.1, 33.4, 33.7; 106/35
See application file for complete search history.

(56) References Cited

U.S. PATENT DOCUMENTS

| 3,710,278 | A | * | 1/1973 | Hopkins et al. ............... 372/41 |
| 4,748,391 | A | * | 5/1988 | Sigai et al. .................. 313/486 |
| 4,794,094 | A | * | 12/1988 | Makishima et al. ........... 501/5 |
| 4,988,882 | A | * | 1/1991 | Francois et al. ......... 250/483.1 |
| 5,952,253 | A | | 9/1999 | Dejneka et al. |
| 6,489,531 | B1 | * | 12/2002 | Carpena et al. ................ 588/2 |
| 2005/0244449 | A1 | * | 11/2005 | Sayer et al. ................. 424/422 |

FOREIGN PATENT DOCUMENTS

DE    44 23 793 C1    2/1996

OTHER PUBLICATIONS

Ito, "Silicate Apatites and Oxyapatites," *The American Mineralogist* 53:890-907 (1968).

* cited by examiner

Primary Examiner—Karl Group
(74) Attorney, Agent, or Firm—Nixon Peabody LLP

(57) ABSTRACT

Apatite glass ceramic which contains at least one glass phase and at least one apatite phase and is characterized in that at least one of the apatite phases is a phosphate- and fluorine-free siliceous oxyapatite phase.

26 Claims, 3 Drawing Sheets

APATITE GLASS CERAMIC BASED ON SILICEOUS OXYAPATITES

Figure 1:
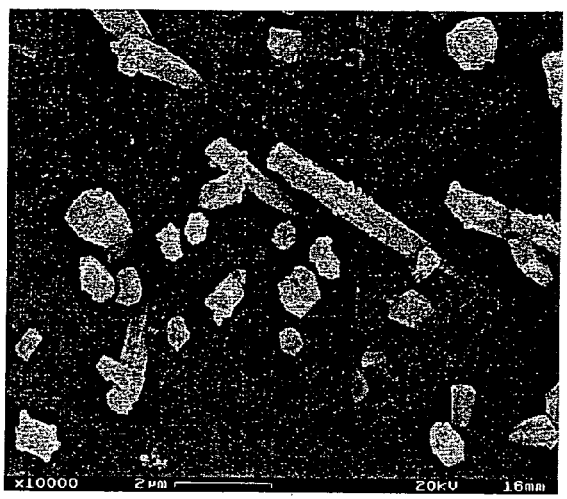

The invention relates to apatite glass ceramics which contain siliceous oxyapatite as crystal phase. These glass ceramics are particularly suitable for a use in dental technology because of their physical and chemical properties.

Apatite is a phosphate-containing mineral with the general formula $Ca_{10}(PO_4)_6(OH,F,Cl)_2$. Hydroxyapatite, $Ca_5(PO_4)_3OH$, is the main constituent of the enamel of teeth and of the solid substance of bones, proportions of $CO_3^{2-}$ also being included. In the specialist scientific literature of crystallography there are also however, e.g. in Jun Ito, The American Mineralogist 53 (1968) 890, descriptions of apatites which are phosphate- and fluorine-free. This is unusual at first glance, but can be explained by isotopic or even isomorphic relationships between phosphates and silicates. These phosphate-free apatites are called siliceous oxyapatites.

Glass ceramics which contain phosphate- and fluorine-free siliceous oxyapatite crystals have not been described until now. Previously only materially related apatite-containing glass ceramics were known, which are presented in the following.

In dental medicine, leucite-containing glass ceramics which can contain needle-shaped apatite crystals were developed for restorative dental prosthetics, for the production of inlays, crowns, bridges and veneer facings.

DE 44 23 793 discloses leucite-containing phosphosilicate glass ceramics which, as well as a leucite-crystal phase, contain at least one further crystal phase and one or more glass phases. Glass ceramics which contain phosphate-containing, needle-shaped apatite crystals as a further crystal phase are preferred.

Transparent glass ceramics are known from U.S. Pat. No. 5,952,253, which contain apatite crystals as crystalline phase. The glass ceramics have a relatively high $Al_2O_3$ content and less than 20 vol.-% apatite crystals. These apatite crystals can contain silicate, but have no oxygen ions in the (OH, F, Cl) position and thus cannot be called siliceous oxyapatites. The glass ceramics are said to be suitable in particular for polarisation-sensitive applications, such as magnifying lenses and lasers. Because of their complete optical transparency they are not suitable for dental applications.

DE 103 40 597 relates to translucent, radio-opaque phosphosilicate glass ceramics with improved optical properties, in particular with a selectively settable translucency and optical brightness, which contain needle-shaped, phosphate-containing apatite crystals and leucite crystals. Both crystal phases form from a starting glass without addition of another glass ceramic composition. These glass ceramics are characterized in that optically they come very close to the properties of natural human teeth.

Translucent apatite glass ceramics with phosphate- and fluorine-free siliceous oxyapatite crystals whose linear thermal expansion coefficients can be varied within a large range and which have a selectively settable translucency are thus not yet known according to the state of the art.

The object of the invention is to provide glass ceramics, whose linear thermal expansion coefficient can be varied within a large range, whose optical properties are selectively settable and which moreover have a high chemical resistance and good processing properties on very different substrate materials.

This object is achieved by apatite glass ceramics with at least one glass phase and at least one apatite phase which are characterized in that at least one of the apatite phases is a phosphate- and fluorine-free siliceous oxyapatite phase. The degree of opacity of the glass ceramics can be set by varying the size and the proportion of the apatite crystals. Glass ceramics which contain 1 to 8 and in particular 1 to 3 different fluorine-free siliceous oxyapatite phases are preferred.

By siliceous oxyapatites is meant crystal phases which have $[SiO_4]$ tetrahedra instead of $[PO_4]$ tetrahedra in the crystal structure of the apatite and the (OH, F, Cl) positions of which are occupied by oxygen ions.

The oxyapatite crystals thus not only contain no phosphate but are thus also fluorine-free. In contrast the glass phase of the glass ceramic can contain fluorine and also phosphate.

The opacity of the apatite glass ceramics according to the invention can be set in a range from 0.3 to 0.96, measured according to BS (British Standard) 5612-1978. The glass ceramics thus have a translucency and an opacity which correspond to a large degree to those of natural teeth.

Preferred are apatite glass ceramics which contain exclusively phosphate- and fluorine-free siliceous oxyapatites as apatite phase(s). By phosphate- and fluorine-free siliceous oxyapatites is meant in particular silicates of the general formula $Me[I]_xMe[II]_yMe[III]_z(SiO_4)_6O_2$, where Me[I] in each case represents a monovalent cation, Me[II] in each case a divalent, and Me[III] in each case a trivalent cation and x, y and z are chosen so that the sum of the valences of the mono-, di- and trivalent cations gives a value of 28. The indices x, y and z can assume the value 0, but at least one of these indices must always be different from 0. These crystal phases are also called siliceous oxyapatites in the following for the sake of simplicity.

Me[I], Me[II] and Me[III] are preferably metal cations, quite particularly preferred is Me[I] Na or Li, Me[II] Ca or Sr and Me[III] Y or La.

According to the invention particularly preferred apatite glass ceramics are those which contain one or more oxyapatite phases of the formula $Me[I]Me[III]_9(SiO_4)_6O_2$, $Me[II]_2Me[III]_8(SiO_4)_6O_2$ and/or $Me[III]_{9.33}(SiO_4)_6O_2$, quite particularly those which contain one or more siliceous oxyapatite phases of the formula $NaY_9(SiO_4)_6O_2$, $LiY_9(SiO_4)_6O_2$, $Sr_2Y_8(SiO_4)_6O_2$, $Ca_2Y_8(SiO_4)_6O_2$, $Sr_2La_8(SiO_4)_6O_2$ and/or $La_{9.33}(SiO_4)_6O_2$.

As well as the siliceous oxyapatite crystal phase(s) the apatite glass ceramics according to the invention can contain one or more, preferably 1 to 8, particularly preferably 1 to 3 further crystal phases. As further crystal phase leucite ($KAlSi_2O_6$) is preferred in particular. Particularly preferred glass ceramics according to the invention contain one or more differently composed fluorine-free siliceous oxyapatite crystal phases, quite particularly preferably 1 to 3 fluorine-free siliceous oxyapatite crystal phases, and 1 to 2 leucite phases.

The glass ceramics according to the invention preferably contain 1 to 8, particularly preferably 1 to 2 glass phases.

The crystal phase is detected through scanning electron microscope (SEM) pictures and room-temperature X-ray diffraction (RT-XRD) analyses.

The apatite glass ceramics according to the invention preferably contain the following components, all percentages, unless specified otherwise, relating to the total mass of the glass ceramic:

| | |
|---|---|
| SiO$_2$ | 40 to 70 wt.-% |
| B$_2$O$_3$ | 0 to 9 wt.-% |
| Al$_2$O$_3$ | 7 to 15 wt.-% |
| Y$_2$O$_3$ | 0 to 14 wt.-% |
| La$_2$O$_3$ | 0 to 17 wt.-% |
| ZrO$_2$ | 0 to 3 wt.-% |
| LiO$_2$ | 0 to 8 wt.-% |
| Na$_2$O | 0 to 24 wt.-% |
| K$_2$O | 0 to 14 wt.-% |
| CaO | 0 to 9 wt.-% |
| SrO | 0 to 15 wt.-% |
| F | 0 to 3 wt.-%. |

The following preferred ranges of quantities, which can be chosen independently of each other, exist for these components:

| | |
|---|---|
| SiO$_2$ | 45.9 to 64.0 wt.-% |
| B$_2$O$_3$ | 0 to 8.5 wt.-% |
| Al$_2$O$_3$ | 7.9 to 14.3 wt.-% |
| Y$_2$O$_3$ | 0 to 12.0 wt.-% |
| La$_2$O$_3$ | 0 to 14.9 wt.-% |
| ZrO$_2$ | 0 to 1.7 wt.-% |
| LiO$_2$ | 0 to 6.0 wt.-% |
| Na$_2$O | 0 to 20.0 wt.-% |
| K$_2$O | 0 to 11.6 wt.-% |
| CaO | 0 to 7.3 wt.-% |
| SrO | 0 to 12.8 wt.-% |
| F | 0 to 2.2 wt.-%. |

For apatite glass ceramics with a high degree of turbidity, compositions are preferred in which the sum of the masses of the components Al$_2$O$_3$, Y$_2$O$_3$ and La$_2$O$_3$ is 12.9 to 25.9 wt.-% relative to the total mass of the glass ceramic.

Moreover apatite glass ceramics are preferred in which the sum of the masses of the components Li$_2$O, Na$_2$O and K$_2$O is 10.5 to 20.0 wt.-%.

It is advantageous for the properties of the apatite glass ceramic if the proportion of apatite crystals is at least 5 wt.-%, preferably 10 to 35 wt.-%.

It is advantageous for the properties of the apatite glass ceramic if the proportion of further crystal phases, preferably leucite, is more than 5 wt.-%, preferably 10 to 70 wt.-%.

The apatite crystals themselves are preferably needle-shaped and have according to a further preferred embodiment an average length of 0.1 to 10 μm, relative to the number of crystals.

The apatite crystals preferably have an average aspect ratio of 0.1 to 100, relative to the number of crystals. The aspect ratio is the ratio of the average crystal length to the average crystal diameter.

The apatite glass ceramics according to the invention can be used as opacifying component preferably for sintered glass ceramics in the dental field. They are also suitable as coating or facing materials for substrates, such as dental suprastructures based on ceramic and glass ceramic materials. They have a settable linear thermal expansion coefficient (TEC) and are thus suitable for various substrate materials.

Dental restorations usually consist of a substructure onto which a facing material, which replaces the actual hard tooth substance, is applied in one or more sintering processes. A range of materials may be considered as substructure materials, above all differently composed metal alloys, but also formed workpieces made of zirconium oxide ZrO$_2$, aluminium oxide Al$_2$O$_3$ as well as high-strength glass ceramics, e.g. based on lithium disilicate. Dental restorations range from single crowns to major restorations, which can replace the entire dental arch. Which material is applied in which reconstruction is determined essentially by the indication. The production of an artificial denture using ceramic materials generally requires a matching of the properties of the facing materials to the substructure materials, to obtain mechanical properties that are adequate for the planned use.

Because of the wide range of substructure materials, facing materials are required the properties of which can be varied over a wide range. An important parameter is the sintering- or firing temperature of the facing material, which must be adapted to the substructure material, in order to prevent deformations resulting from too high a thermal load. A firing temperature which is too low can in contrast lead to inadequate adhesion.

Another important parameter is the linear thermal expansion coefficient. The optimal bond between substructure and layers subsequently fired on is achieved by the correct matching of the linear thermal expansion behaviour of the facing material to the substructure material. The range for the thermal expansion coefficient is defined by aluminium oxide Al$_2$O$_3$ (TEC ca. $6.9 \cdot 10^{-6}$ K$^{-1}$) and high-gold casting alloys (TEC ca. $16.0 \cdot 10^{-6}$ K$^{-1}$).

The wetting of the substrate by the facing material at high temperatures is not to be disregarded with regard to the bonding behaviour. Insufficient wetting can cause the layer material to peel off, which leads to the failure of the reconstruction under masticatory load.

Because dental materials in the oral cavity are constantly exposed to a multiplicity of chemical influences, such as for example acid fluids, their chemical resistance (measured according to ISO 9693) is accorded great importance. The acid resistance serves as a measure of the chemical resistance of glass ceramics in the dental field.

Moreover the bending strength (measured according to ISO 6872) is important for clinical use.

The prosthetic replacement of the hard tooth substance moreover requires the individual matching of the reconstruction to the particular clinical situation of the patient. To this end, the different ceramic facing materials must have a defined translucency (ΔCR).

The glass ceramics according to the invention allow the targeted setting of the above-mentioned parameters firing temperature, linear thermal expansion coefficient (TEC), moistening, chemical solubility, bending strength and translucency through the choice of different compositions and/or the variation of their thermal treatment.

The TEC is set through the targeted changing of the chemical composition of the apatite glass ceramic according to the invention within the ranges mentioned and the targeted control of the crystallization. The effect of the targeted variation of the leucite-forming components K$_2$O, Al$_2$O$_3$ and SiO$_2$ is for example that, through controlled surface crystallization, leucite crystals are formed which effect an increase in the TEC. The surface crystallization can be accelerated by activation of the glass surface by fine-grinding and production of a glass granulate.

The linear thermal expansion coefficient (TEC) of the apatite glass ceramics according to the invention is in the range of $6 \cdot 10^{-6}$ K$^{-1}$ to $15 \cdot 10^{-6}$ K$^{-1}$ at temperatures of 100 to 500° C. The glass ceramics are thus suitable both for the coating or facing of high-gold dental alloys with a TEC range of 14 to $16 \cdot 10^{-6}$ K$^{-1}$, such as Ag—Au, Au, Au—Pt alloys, as well as for the coating and facing of Al$_2$O$_3$, ZrO$_2$ ceramics, titanium or titanium alloys with TECs in the range of 7 to $12*10^{-6}$ $K^{-1}$ as well as Ag—Pd, Pd and Co—Cr alloys.

The firing-on temperature of the apatite glass ceramics according to the invention can also be varied within a large range and thus adapted to very different substrates. An adaption of the firing temperature can occur through variation of the composition of the glass ceramic or through the use of other glasses or glass ceramics as mixture component(s) for the apatite glass ceramic according to the invention. Apatite glass ceramics which have a firing temperature of 830° C. to 1150° C. are preferred.

The apatite glass ceramics according to the invention preferably have a chemical resistance, measured according to the ISO specification 9693, of <100 µg/cm², particularly preferably <80 µg/cm² and quite particularly preferably 10 to <80 µg/cm².

The apatite glass ceramics according to the invention are also characterized by a controllable translucency, turbidity and a high brightness.

The translucency can be controlled by variation of the chemical composition of the glass ceramic and by variation of the conditions of the thermal treatments. A high translucency and thus a low turbidity is achieved by the formation of small quantities of crystals, i.e of quantities of crystals in the lower range of the crystal contents defined above. Conversely high crystal contents in the glass ceramic produce a high turbidity and low translucency.

The procedure for the production of the glass ceramics according to the invention is preferably that (a) the starting components required for the production of the glass ceramic are mixed and are melted to form a glass, preferably at a temperature in the range of 1200 to 1650° C.

(b) the glass melt from step (a) is transformed into a glass granulate, preferably by pouring the glass melt into water, (c) the glass granulate from step (b) is optionally ground to a glass powder with an average grain size of 1 to 500 µm, relative to the particle count, and (d) then the glass granulate from step (b) or the glass powder from step (c) is subjected to a thermal treatment (single-stage or multistage) in the temperature range of 700 to 1200° C. for a period of 30 minutes to 6 hours per treatment step.

In step (a) firstly the individual components required, such as e.g. carbonates, oxides and fluorides are homogeneously mixed with one another and melted at the temperatures mentioned. In the process the desired starting glass forms, and is then transformed into a glass ceramic.

Then in step (b) the glass melt obtained is quenched by pouring in water. A glass granulate forms. This production step is usually called fritting.

Optionally in step (c) the glass granulate is subsequently comminuted, i.e. preferably ground to the preferred grain size with customary mills. The thus-produced glass powder preferably has an average grain size of 1 to 500 µm, relative to the particle count.

Then in step (d) the glass granulate or where appropriate the glass powder is subjected to a thermal treatment at temperatures of 700 to 1200° C. for a period of 30 minutes to 6 hours, preferably 30 minutes to 3 hours per treatment step. The thermal treatment can take place in one or more steps. Preferably it comprises 1 to 4, in particular 1 or 2 steps. A temperature of 900° C. to 1200° C. is preferred, because it promotes the formation of the siliceous oxyapatite crystals in the form and quantity according to the invention.

A particular advantage of the method according to the invention is that for the first time apatite glass ceramics become available which contain phosphate- and fluorine-free siliceous oxyapatite.

By scanning electron microscope and X-ray diffraction examinations, it was possible to show that siliceous oxyapatites represent the main crystal phase of the apatite glass ceramics according to the invention. The crystallite size can be controlled by different thermal treatments (single- or multi-stage, different temperatures). In addition it was surprisingly found, that by targeted changing of the chemical composition and by using different crystallization mechanisms, in addition to the siliceous oxyapatite crystals, the formation of further crystal phases can be stimulated.

First systematic studies of the growth processes of the oxyapatite crystals indicate that a surface growth mechanism is involved. Because e.g. leucite also is formed according to the mechanism of surface crystallization, a double, controlled surface crystallization, not previously observed in glass ceramics according to the state of the art takes place with leucite-containing, apatite glass ceramics according to the invention.

For the further processing of the glass ceramics, these are preferably moistened in powder form with water or another suitable solvent, formed and then fired. According to a likewise preferred, alternative processing method the glass ceramics in powder form are initially sintered to produce mouldings which can, for the further forming, be pressed hot in viscous state or mechanically worked by CAD/CAM processes at room temperature.

The glass ceramics according to the invention are characterized by a surprisingly good miscibility with other glasses and/or glass ceramics. For this reason the above-mentioned parameters such as firing temperature, linear thermal expansion coefficient (TEC), wetting, chemical solubility, bending strength, translucency and turbidity can also be set in a simple manner by a mixing sequence. For this, one or more glass ceramics according to the invention are mixed with one or more other glasses and/or glass ceramics. The mixing of two or more glass ceramics according to the invention is also possible. Each of these mixtures is a mixed glass ceramic which contains at least one glass ceramic according to the invention. As further components for mixing with the glass ceramic or glass ceramics according to the invention, glasses or glass ceramics are suitable, depending on which properties are sought. The production of the mixed glass ceramics comprises the steps:

(A) Production of a glass ceramic according to the invention, preferably according to the steps (a) to (d) described above, (B) Production of another glass powder with a different composition or another glass ceramic powder with a different composition and (C) Mixing of the components from steps (A) and (B).

(D) Optionally the thus-obtained mixture can subsequently be thermally treated subsequently, in order to ensure the homogeneity of the mixture.

(E) The powder mixture can be sintered to produce compact bodies or alternatively pressed and/or sintered to produce monolithic bodies.

Such mixed glass ceramics represent an important field of application for the apatite glass ceramics according to the invention. The mixed glass ceramics are characterized in that they contain phosphate- and fluorine-free crystals of the siliceous oxyapatite type. A subject of the invention are also multi-component materials which, as first component, contain at least one apatite glass ceramic according to the invention in powder form and, as second component, at least one other glass-and/or glass ceramic powder. These materials can be transformed into mixed glass ceramics in the way described above and allow, by simple measuring out of components 1 and 2, the production of a mixed glass ceramic which has for example a specific TEC.

The phosphate-free apatite glass ceramics according to the invention are freely miscible with practically all glasses and glass ceramics, whereby mixed glass ceramics with siliceous oxyapatite phases are produced. However it is also possible to mix the apatite glass ceramic according to the invention with silico-phosphate glasses in powder or granulate form without the phosphate-free, siliceous oxyapatite in the glass ceramic according to the invention being destroyed in the subsequent sintering.

The further glass ceramic or ceramics which are as mixing component added to the glass ceramics according to the invention can be glass ceramics according or not according to the invention. Preferred glasses and glass ceramics not according to the invention for combining with the glass ceramics according to the invention are silicate, borate, phosphate or aluminosilicate glasses and glass ceramics. Particularly preferred are $SiO_2$—$Al_2O_3$—$K_2O$ (with cubic or tetragonal leucite crystals), $SiO_2$—$B_2O_3$—$Na_2O$, alkali silicate, alkali-zinc-silicate, silicophosphate and/or $SiO_2$—$ZrO_2$ glasses and glass ceramics. These mixtures preferably contain 5 to 90 wt.-% glass ceramic according to the invention and 5 to 90 wt.-% glasses and/or glass ceramics which are not according to the invention. In the resulting mixed glass ceramics the oxyapatite crystals content is preferably in the range of 1 to 35 wt.-%.

Particularly suitable glasses and glass ceramics as well as their production are described in DE 43 14 817, DE 44 23 793, DE 44 23 794, DE 196 47 739, DE 197 25 552, DE 197 25 553, DE 197 25 555, DE 100 31 431 and in particular in DE 44 28 839, which are incorporated herein by reference.

Sintered or monolithic bodies can of course also be obtained by using one or more glass ceramic powders according to the invention without adding non-inventive glasses or glass ceramics.

A glass which is particularly preferred as second component is an alkali-zinc silicate glass which contains the following components:

| | |
|---|---|
| $SiO_2$ | 52.0 to 63.5 wt.-% |
| Me'[III]$_2$O$_3$ | 8.5 to 13.0 wt.-% |
| $K_2O$ | 0 to 20.5 wt.-% |
| $Na_2O$ | 1.5 to 20.0 wt.-% |
| $LiO_2$ | 0 to 5.0 wt.-% |
| ZnO | 2.0 to 8.0 wt.-% |
| Me'[II]O | 2.5 to 6.5 wt.-% |
| $TiO_2 + ZrO_2$ | 0.5 to 6.0 wt.-% |
| $SnO_2$ | 0 to 9.5 wt.-% |
| $P_2O_5$ | 0 to 4.0 wt.-% |
| F | 0 to 2.0 wt.-% |
| $CeO_2$ | 0 to 3.0 wt.-%, | where
(a) Me'[III]$_2$O$_3$ is formed by 0 to 13 wt.-% $Al_2O_3$ and 0 to 9.5 wt.-% $La_2O_3$ and
(b) Me'[II]O is formed by 0 to 3.5 wt.-% CaO, 0 to 4.5 wt.-% BaO and 0 to 5.0 wt.-% MgO.

The production of this glass is described in DE 44 28 839.

For the combination with the glass ceramics according to the invention, glasses and glass ceramics with the compositions given below are quite particularly suitable:

Potassium-zinc-silicate glass sintering at low temperature (DE 100 31 431):

| Component | Proportion [in wt.-%] |
|---|---|
| $SiO_2$ | 60.0–72.0 |
| $Li_2O$ | 1.0–5.0 |
| $K_2O$ | 10.0–23.0 |
| ZnO | 8.5–20.0 |

Apatite glass ceramic sintering at low temperature (DE 100 31 430):

| Component | Proportion [wt.-%] |
|---|---|
| $SiO_2$ | 56.0–65.0 |
| $Li_2O$ | 1.8–5.3 |
| $K_2O$ | 9.0–17.5 |
| ZnO | 9.0–16.0 |
| CaO | 3.5–10.5 |
| $P_2O_5$ | 2.0–6.0 |
| F | 0.5–1.0 |

Translucent apatite glass ceramic (DE 197 25 555/DE 197 25 553):

| Component | Proportion [wt.-%] |
|---|---|
| $SiO_2$ | 45.0–70.0 |
| $Al_2O_3$ | 5.0–22.0 |
| $K_2O$ | 3.0–8.5 |
| $Na_2O$ | 4.0–13.0 |
| CaO | 1.5–11.0 |
| $P_2O_5$ | 0.5–6.5 |
| F | 0.1–2.5 |

Alkali silicate glass (DE 197 25 552):

| Component | Proportion [wt.-%] |
|---|---|
| $SiO_2$ | 55.0–71.0 |
| $Al_2O_3$ | 5.0–16.0 |
| $B_2O_3$ | 0.2–10.0 |
| $K_2O$ | 4.5–10.0 |
| $Na_2O$ | 3.0–14.0 |

Sinterable lithium disilicate glass ceramic (DE 196 47 739):

| Component | Proportion [wt.-%] |
|---|---|
| $SiO_2$ | 57.0–80.0 |
| $Al_2O_3$ | 3.0–5.0 |
| $La_2O_3$ | 0.1–6.0 |
| $Li_2O$ | 11.0–19.0 |

ZrO$_2$—SiO$_2$ glass ceramic (DE 44 23 794):

| Component | Proportion [wt.-%] |
|---|---|
| SiO$_2$ | 42.5–58.5 |
| Li$_2$O | 7.0–14.5 |
| P$_2$O$_5$ | 4.0–13.5 |
| ZrO$_2$ | 15.0–28.0 |

Leucite-containing phosphosilicate glass ceramic (DE-44 23 793):

| Component | Proportion [wt.-%] |
|---|---|
| SiO$_2$ | 49.0–57.5 |
| Al$_2$O$_3$ | 11.4–21.0 |
| P$_2$O$_5$ | 0.5–5.5 |
| CaO | 2.5–11.5 |
| K$_2$O | 9.0–22.5 |
| Na$_2$O | 1.0–9.5 |
| ZrO$_2$ | 0.8–8.5 |
| F | 0.25–2.5 |

Opalescet glass (DE 43 14 814):

| Component | Quantity [wt.-%] |
|---|---|
| SiO$_2$ | 48.0–66.0 |
| Me$^{III}_2$O$_3$ | 5.0–20.0 |
| Me$^I_2$O | 6.0–22.0 |
| Me$^{II}$O | 3.5–16.0 |
| Me$^{IV}$O$_2$ | 0.5–10.0 |
| P$_2$O$_5$ | 0.5–5.0 |

The glass ceramics obtained by mixing the glass ceramics according to the invention with the above-named glasses and glass ceramics are also a subject of the invention.

As well as the named components, the glass ceramics and mixed glass ceramics according to the invention can advantageously contain one or more chromophoric or fluorophoric oxides of metals which are preferably selected from the group of the 3d and 4f elements of the periodic table of the elements in particular one or more oxides of the metals Zr, Ta, Yb, Nb, Tb, La, Er, Pr, Ce, Ti, V, Fe and Mn. These oxides are incorporated into the glass structure.

The apatite glass ceramics according to the invention are particularly suitable as dental materials and for the production of dental materials, in particular coating materials or facing materials, and for the production of dental restorations, in particular crowns, bridges, partial crowns, onlays, artificial teeth, stump superstructures or facets. Moreover the apatite glass ceramics according to the invention are also suitable in particular as an opacifying component for dental composites, opaquer materials etc.

Figure 2:
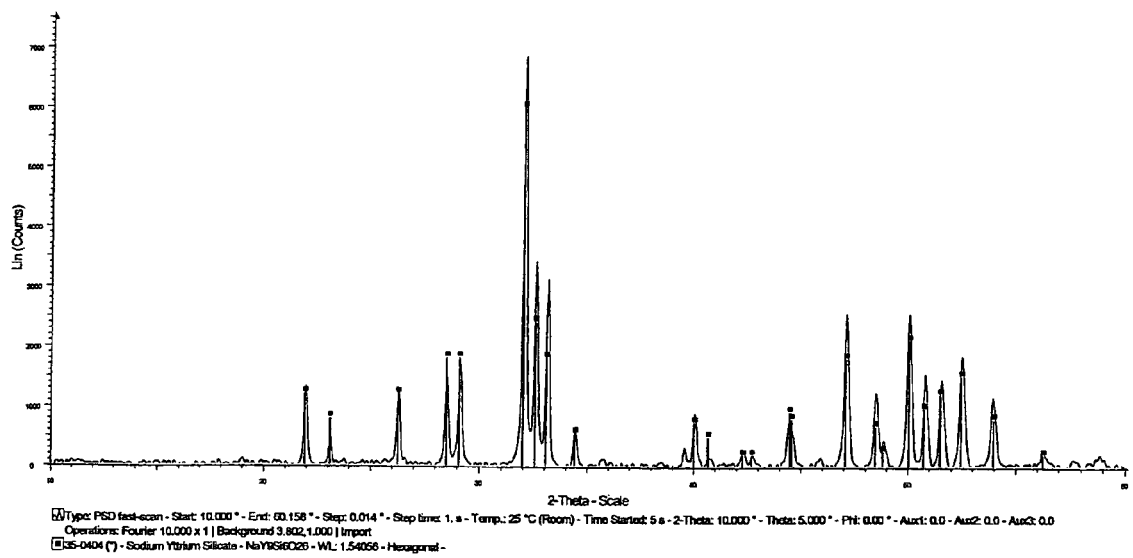
Figure 3:
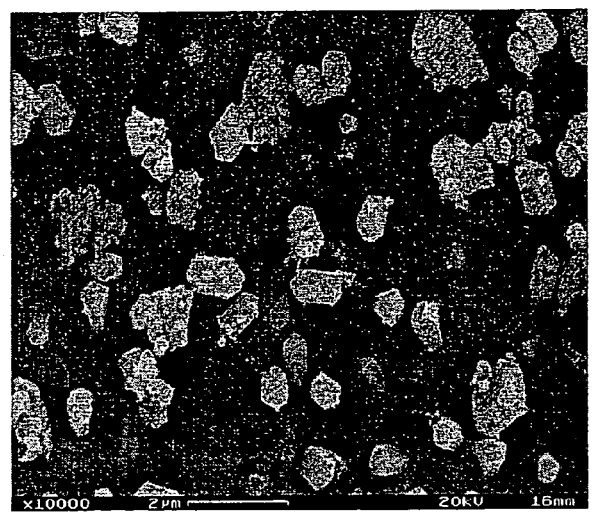
Figure 4:
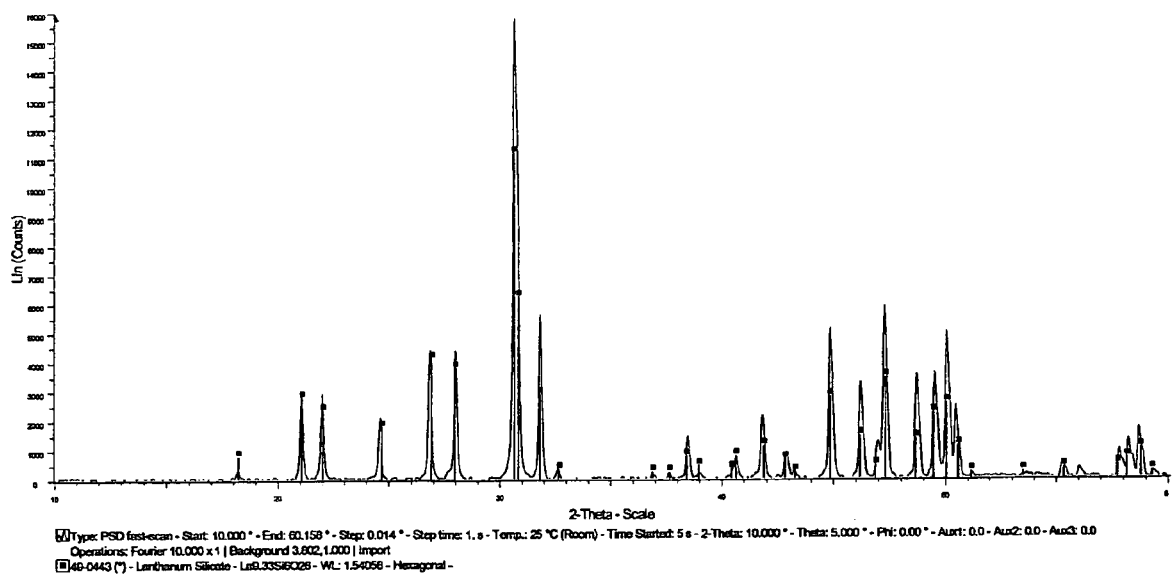
Figure 5:
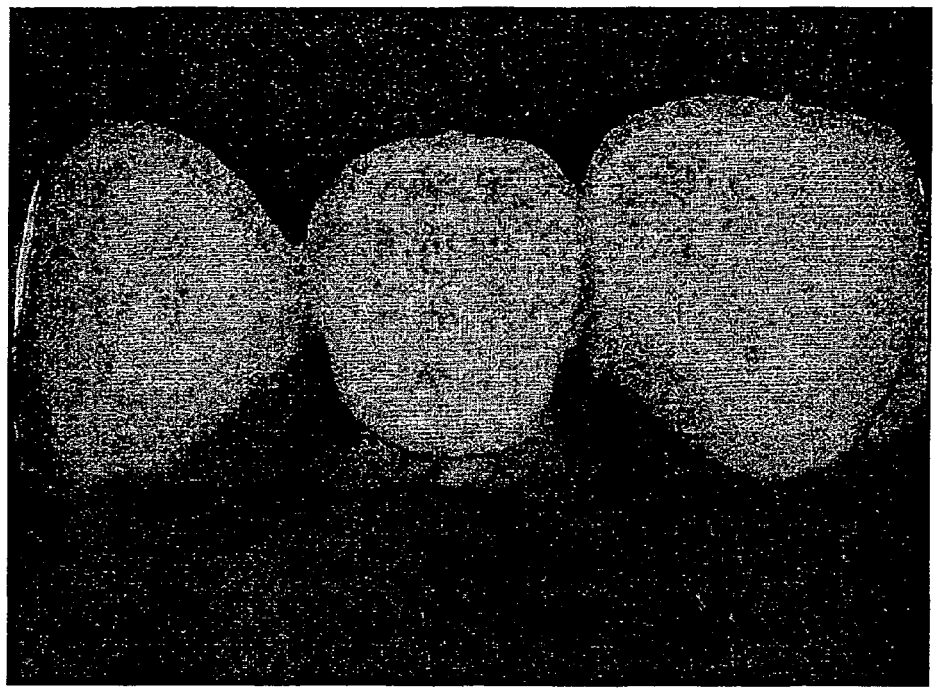
Figure 6:
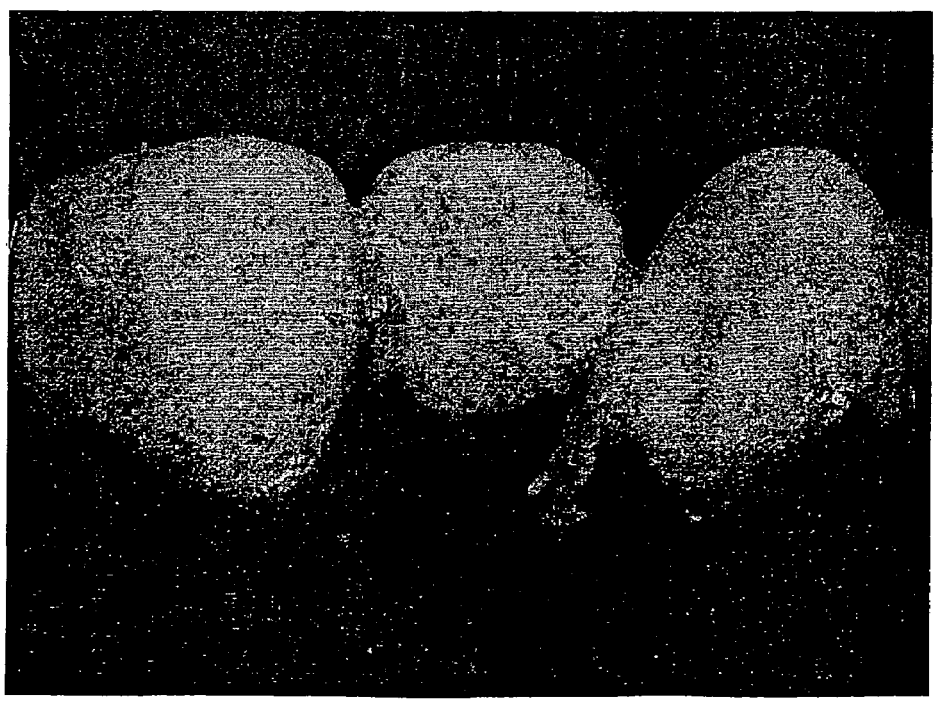

The invention is described in more detail in the following with the help of examples and figures, where FIG. 1 shows an electron microscopic picture of a glass ceramic according to the invention with NaY$_9$(SiO$_4$)$_6$O$_2$ crystal phase, FIG. 2 shows an X-ray diffraction diagram of the glass ceramic from FIG. 1, FIG. 3 shows an electron microscopic picture of another glass ceramic according to the invention with NaY$_9$(SiO$_4$)$_6$O$_2$ crystal phase, FIG. 4 shows an X-ray diffraction diagram of the glass ceramic from FIG. 3, FIG. 5 shows a dental restoration faced with a mixed glass ceramic according to the invention as seen from the labia and FIG. 6 shows the same dental restoration as seen from the palate.

EXAMPLES

Examples 1 to 17

Production of Apatite Glass Ceramics

In total 17 different glass ceramics according to the invention were produced by preparing a homogeneous mixture of the raw materials required to obtain the compositions mentioned in Table I and processing the mixture to a glass melt at temperatures of 1550° C. The glass melt obtained was poured into a waterbath and the glass granulate obtained was ground to an average grain size of <90 μm. The glass powder was then subjected to a two-stage thermal treatment at 800° C. (1 hour) and 1050° C. (30 minutes).

The glass ceramics were then further examined by scanning electron microscopy and X-ray diffusion analysis. The crystal phases found in so doing are also shown in Table I. FIG. 1 shows an electron scanning microscope picture of the glass ceramic from Example 2, FIG. 3 a picture of the glass ceramic from Example 12. In FIG. 2 an X-ray diffraction diagram of the glass ceramic from Example 2 is shown, in FIG. 4 an X-ray diffraction diagram of the glass ceramic from Example 12. The crystal phases were determined according to the JCPDS register, which constitutes a comprehensive database for X-ray diffraction diagrams of crystalline compounds. The respective references according to this register are drawn in in FIG. 2 and FIG. 4 as so-called streak diagrams. Thus FIG. 2 contains the reference diffractogram 35-0404 for NaY$_9$Si$_6$O$_{26}$ [NaY$_9$(SiO$_4$)$_6$O$_2$]. The agreement with the established diffractogram of the apatite glass ceramic according to the invention is unequivocal.

TABLE I

Composition of apatite glass ceramics

| | Example | | | |
|---|---|---|---|---|
| Oxide | 1 wt. % | 2 wt.-% | 3 wt.-% | 4 wt.-% |
| SiO$_2$ | 46.7 | 48.9 | 47.5 | 47.5 |
| B$_2$O$_3$ | 7.3 | 7.9 | 7.7 | 7.7 |
| Al$_2$O$_3$ | 9.8 | 10.5 | 10.2 | 10.2 |
| Y$_2$O$_3$ | — | 11.1 | 10.8 | 10.8 |
| La$_2$O$_3$ | 14.9 | — | — | — |

TABLE I-continued

Composition of apatite glass ceramics

| | | | | |
|---|---|---|---|---|
| $ZrO_2$ | — | — | — | — |
| $Li_2O$ | — | — | — | — |
| $Na_2O$ | 6.6 | 7.1 | 6.9 | 6.9 |
| $K_2O$ | 10.0 | 10.7 | 10.5 | 10.5 |
| CaO | — | — | — | — |
| SrO | 4.1 | — | 5.7 | 5.7 |
| F | 0.6 | 0.7 | 0.7 | 0.7 |
| Cryst. phase | $La_{9.33}(SiO_4)_6O_2$ | $NaY_9(SiO_4)_6O_2$ | $NaY_9(SiO_4)_6O_2$ | $NaY_9(SiO_4)_6O_2$ |

| | Example | | | |
|---|---|---|---|---|
| Oxide | 5 wt.-% | 6 wt.-% | 7 wt.-% | 8 wt.-% |
| $SiO_2$ | 49.2 | 46.4 | 51.1 | 53.3 |
| $B_2O_3$ | 7.9 | 7.4 | 3.9 | — |
| $Al_2O_3$ | 10.5 | 9.9 | 10.9 | 11.3 |
| $Y_2O_3$ | 11.1 | 10.5 | 11.5 | 12.0 |
| $La_2O_3$ | — | — | — | — |
| $ZrO_2$ | — | — | — | — |
| $Li_2O$ | — | — | — | — |
| $Na_2O$ | 2.7 | 2.6 | 7.4 | 7.7 |
| $K_2O$ | 10.8 | 10.2 | 11.2 | 11.6 |
| CaO | 7.1 | — | 3.3 | 3.4 |
| SrO | — | 12.4 | — | — |
| F | 0.7 | 0.6 | 0.7 | 0.7 |
| Cryst. phase | $NaY_9(SiO_4)_6O_2$ | $NaY_9(SiO_4)_6O_2$ | $NaY_9(SiO_4)_6O_2$ leucite | $NaY_9(SiO_4)_6O_2$ leucite |

| | Example | | | |
|---|---|---|---|---|
| Oxide | 9 wt.-% | 10 wt.-% | 11 wt.-% | 12 wt.-% |
| $SiO_2$ | 51.0 | 48.00 | 49.9 | 45.9 |
| $B_2O_3$ | 8.2 | 7.7 | 8.0 | 7.2 |
| $Al_2O_3$ | 10.9 | 10.2 | 14.3 | 9.6 |
| $Y_2O_3$ | 11.5 | 10.8 | 11.3 | — |
| $La_2O_3$ | — | — | — | 14.7 |
| $ZrO_2$ | — | — | — | 1.6 |
| $Li_2O$ | — | — | 2.4 | — |
| $Na_2O$ | — | — | — | 6.5 |
| $K_2O$ | 11.1 | 10.5 | 10.9 | 9.9 |
| CaO | 7.3 | — | 3.2 | — |
| SrO | — | 12.8 | — | 4.0 |
| F | — | — | — | 0.6 |
| Cryst. phase | $Ca_2Y_8(SiO_4)_6O_2$ | $Sr_2Y_8(SiO_4)_6O_2$ | $LiY_9(SiO_4)_6O_2$ | $La_{9.33}(SiO_4)_6O_2$ |

| | Example | | | | |
|---|---|---|---|---|---|
| Oxide | 13 wt.-% | 14 wt.-% | 15 wt.-% | 16 wt.-% | 17 wt.-% |
| $SiO_2$ | 48.1 | 55.0 | 61.0 | 64.0 | 56.0 |
| $B_2O_3$ | 7.7 | — | — | — | 8.5 |
| $Al_2O_3$ | 10.3 | 6.0 | 8.4 | 8.8 | 7.9 |
| $Y_2O_3$ | 10.9 | 10.0 | 5.0 | 5.3 | 5.0 |
| $La_2O_3$ | — | — | — | — | — |
| $ZrO_2$ | 1.7 | — | — | — | — |
| $TiO_2$ | — | — | — | — | — |
| $Li_2O$ | 6.9 | 20.0 | — | 6.0 | — |
| $Na_2O$ | 10.6 | — | 8.8 | — | 7.8 |
| $K_2O$ | 3.1 | 7.2 | 8.8 | 9.4 | 7.8 |
| CaO | — | — | 6.0 | 4.3 | 5.0 |
| SrO | — | — | — | — | — |
| F | 0.7 | 1.8 | 2.0 | 2.2 | 2.0 |
| Cryst. phase | $NaY_9(SiO_4)_6O_2$ | $NaY_9(SiO_4)_6O_2$ | $NaY_9(SiO_4)_6O_2$ leucite | $LiY_9(SiO_4)_6O_2$ leucite | $NaY_9(SiO_4)_6O_2$ |

The optical and physical properties of some glass ceramics are summarized in Table II. These properties were established in the manner described in Example 18. The TEC of the glass ceramics shown ranges from $6.5*10^{-6}$ $K^{-1}$ (Example 9) to $14.1*10^{-6}$ $K^{-1}$ (Example 6), the firing temperatures from 830° C. (Example 11) to 1160° C. (Example 9).

The glass ceramics of Examples 1, 4, 8, 9 and 11 are, because of their lower TEC-values, particularly suitable for the coating and facing of $Al_2O_3$ ceramics, $ZrO_2$ ceramics, titanium or titanium alloys and lithium disilicate glass ceramics with a low TEC-range of 7 to $12*10^{-6}$ $K^{-1}$ (see Table II), the glass ceramics of Examples 7 and 8 are, because of their high TEC-values, particularly suitable for the coating or facing of high-gold dental alloys with a high TEC-range of 14 to $16*10^{-6}$ $K^{-1}$. (see Table II)

TABLE II

Properties of selected glass ceramics

| Parameter | Example | | | | | | |
|---|---|---|---|---|---|---|---|
| | 1 | 4 | 7 | 8 | 9 | 10 | 11 |
| Melting conditions | 1550° C. for 2 h | | | | | | |
| Optical characteristics after quenching | transparent | | | | | | |
| Annealing conditions | 800° C. for 1 h and 1050° C. for 0.5 h | | | | | | |
| Optical characteristics after annealing | marked turbidity and high brightness | | | | | | |
| Firing temp. [° C.] | 850 | —[4] | 1010 | 1110 | 1010 | 1160 | 870 |
| TEC[1] [$10^{-6}$ $K^{-1}$] | 9.7[1] | 9.5[2] | 14.1[1] | 13.3[1] | 7.1[2] | 6.5[2] | 9.4[1] |
| Tg[2] [° C.] | 575 | 601 | 533 | 589 | 666 | 648 | 580 |
| Chem. resistance[5] | —[4] | —[4] | 53.7 | 41.0 | —[4] | —[4] | 42.9 |

[1]Temperature range: 100–500° C.
[2]Temperature range: 100–600° C.
[3]Transformation temperature
[4]not established
[5]Measured in accordance with ISO 9693

Example 18

Production of a Facing Material Based on a Mixed Glass Ceramic

A mixing sequence comprising several two-component mixed glass ceramics was produced. The compositions of the mixed glass ceramics were selected such that, by variation of the proportions of the mixture components, a systematic variation of the properties resulted. The study also included the boundary members of the mixing sequence, i.e. the pure components A and B. The glass ceramic from Example 7 served as component A, and as component B a glass of the following composition, which was produced according to DE 44 28 839 (all figures in wt.-%):

TABLE III

Composition of the glass B

| Component | Proportion |
|---|---|
| $SiO_2$ | 63.5 wt.-% |
| $Al_2O_3$ | 8.8 wt.-% |
| $K_2O$ | 9.6 wt.-% |
| $Na_2O$ | 6.8 wt.-% |
| $LiO_2$ | 0.8 wt.-% |
| ZnO | 2.4 wt.-% |
| CaO | 3.5 wt.-% |
| $TiO_2$ | 0.4 wt.-% |
| $ZrO_2$ | 1.0 wt.-% |
| $P_2O_5$ | 0.4 wt.-% |
| F | 0.8 wt.-% |
| $CeO_2$ | 0.8 wt.-% |
| $B_2O_3$ | 1.2 wt.-% |

The following mixtures were produced, treated thermally and then analyzed:

TABLE IV

Composition of the glass ceramic mixtures analyzed

| Name of the mixture | Proportion of A [wt.-%] | Proportion of B [wt.-%] | Temperature of the thermal treatment [° C.] |
|---|---|---|---|
| M1 | 100.0 | 0.0 | 1020 |
| M2 | 80.0 | 20.0 | 900 |
| M3 | 50.0 | 50.0 | 840 |
| M4 | 20.0 | 80.0 | 770 |
| M5 | 0.0 | 100.0 | 740 |

Within the series M1 to M5 the proportion of glass ceramic A according to the invention decreases while the proportion of glass B increases.

Production, Treatment and Analysis of the Mixtures:

The individual components were weighed in and mixed together thoroughly in accordance with Table IV. Cylindrical, conical green bodies with a height of 35 mm and an average diameter of 40 mm were then produced from the powders by uniaxial pressing (max. 1 bar). These were treated thermally over a period of 1 hour at the temperatures given in Table IV. At the end of this period the sintered bodies were quenched in cold water, dried, mechanically comminuted and sieved out to a grain size of <90 μm.

The glass ceramics according to the invention and the mixed glass ceramics produced from these were subjected to the following tests:

Measurement of Linear Thermal Expansion Coefficient (TEC):

To measure the linear thermal expansion coefficient (TEC), rod-shaped green bodies were produced from the powders of the respective glass ceramics, and sintered in a vacuum firing oven (Programat® P100, Ivoclar Vivadent AG) at a heating-up rate of 60° C./min. and a holding time of 1 minute at the firing temperatures given in Tables II and VI. Then a glaze firing was carried out without vacuum at a final temperature that was 20° C. higher and a holding time of 1 minute. The linear thermal expansion coefficient of the test piece obtained was measured in the temperature range of 100 to 500° C. or 600° C. with a dilatometer (Bähr type 803). The results are shown in Tables II and VI.

Measurement of Chemical Resistance:

The acid resistance was measured according to the ISO specification 9693. For this, small test sheets with a diameter of 12 mm and a thickness of 1 mm were produced by sintering together glass ceramic-powder with a particle size of <90 μm in the vacuum firing oven (Programat® P100, Ivoclar Vivadent AG) The test pieces were sintered for 1 minute at the firing temperatures given in Tables II and VI. Then the small sheets were stored for 16 hours in 4 vol.-% aqueous acetic acid in closed glass vessels at 80° C. The measured loss of mass relative to the surface of the small sheets was determined as a measure of the acid resistance. The results are shown in Tables II and VI.

Measurement of Firing Temperature:

The temperature at which a standard sheet is thoroughly sintered and has a light surface glaze was taken as the firing temperature. The sheet is produced by manual compaction of the powder, moistened with water, in a metal mould (Ø=16 mm, h=1.6 mm) followed by a single firing. The results are shown in Tables II and VI.

Measurement of Bending Strength:

The bending strength was ascertained in the manner described in ISO 6872 in a biaxial test structure. For this purpose, 8 standard sheets made of moistened, manually compacted ceramic were produced by a double firing, and after plane-parallel machining these were polished to a thickness of 1.2 mm. The results are shown in Table VI.

Measurement of Translucency:

The translucency (ΔCR value) was measured according to BS 5612. Green bodies were produced by hydraulic pressing of 2.5 g powder in a standardized mould, and after a double firing these are worked plane-parallel and polished. The results are shown in Table VI.

TABLE VI

Properties of the glass ceramics after firing on dental alloy

| No | Firing temp. [° C.] | TEC[1] [$10^{-6} \cdot K^{-1}$] | Tg[2] [° C.] | Chem. resist.[3] [μg cm$^{-2}$] | Bending str.[4] [Mpa] | Transl.[5] ΔCR |
|---|---|---|---|---|---|---|
| M1 | 990 | 14.1 | 533 | 53.7 | 116 | 0.98 |
| M2 | 960 | 12.9 | 558 | 16.5 | 112 | 0.97 |
| M3 | 890 | 13.1 | 532 | 24.6 | 109 | 0.96 |
| M4 | 850 | 11.1 | 516 | 23.9 | 78 | 0.88 |
| M5 | 840 | 9.2 | 510 | 21.0 | 93 | 0.27 |

[1] linear thermal expansion coefficient in the temperature range of 100 to 500° C.
[2] transformation temperature
[3] chemical resistance in accordance with EN ISO 9693
[4] bending strength in accordance with ISO 6872
[5] translucency measured in accordance with BS 5612-1978

The properties shown in Table VI behave virtually linearly within the mixing sequences depending on the increase or decrease of a component and can therefore be set through the choice of the composition of a mixture.

The results show that firing temperature, linear thermal expansion coefficient (TEC), chemical resistance, bending strength and translucency can be easily set by a mixing sequence, which can be formed from various mixtures for example of two starting components A and B. Each of these mixtures represents a mixed glass ceramic.

Determination of Wetting:

The wetting of the substructure material by the mixtures was examined using mixtures which appeared to be suitable for a given substructure material because of the firing temperature and thermal expansion coefficient. To this end, standardized three-membered front-tooth bridges made of a palladium base alloy, which had the following material characteristics, were chosen as substructure,

TABLE V

Properties and composition of the dental alloy

| Chemical composition [wt. %] | TEC$_{(25-500° C.)}$ [$10^{-6}$ K$^{-1}$] | Density [g cm$^{-3}$] | Solidus point [° C.] |
|---|---|---|---|
| Pd 75.2 | 13.8 | 11.0 | 1270 |
| Au 6.0 | | | |
| Ag 6.5 | | | |
| In 6.0 | | | |
| Ga 6.0 | | | |
| Ru < 1.0 | | | |
| Li < 1.0 | | | |

According to the dental procedure these bridges were conditioned and then prepared for facing with the corresponding mixture by priming with an opaquer. Then the glass ceramic mixture to be applied was slipped with water and applied to the metal substructure. Sintering took place in a dental firing oven under vacuum according to the firing parameters given in Table VI. The opaquer serves to prime and cover the inherent colour of the metal. As opaquers, glass ceramics not according to the invention, to which finely dispersed colouring pigments were added, were sintered onto the metal substrate in a thin layer at 840° C.

In order to be able to assess the degree of wetting, only one sintering process, the so-called main firing, was carried out. The assessment was qualitative and photographically documented. The wetting behaviour of the mixed glass ceramic is represented by the example of the composition M4 in FIG. 5 and FIG. 6. In FIG. 5 a bridge faced with the mixed glass ceramic M4 is shown in labial view, in FIG. 6 the same reconstruction is to be seen in palatal view. It is clear that the ceramic layer material connects intimately with the opaquer layer and wets it completely. The layer material does not peel off either at the thinly spreading edges of the reconstruction or in the interdental area.

The invention claimed is:

1. Apatite glass ceramic comprising at least one glass phase and at least one apatite phase, wherein at least one apatite phase is a phosphate- and fluorine-free siliceous oxyapatite phase, which contains one or more oxyapatite phases of the formula Me[I]$_x$Me[II]$_y$Me[III]$_z$(SiO$_4$)$_6$O$_2$, in which Me[I] represents a monovalent cation, Me[II] a divalent cation and Me[III] a trivalent cation and x, y and z are chosen so that the sum of the valences of the cations Me[I], Me[II] and Me[III] gives the value 28.

2. Apatite glass ceramic according to claim 1, wherein each apatite phase is a phosphate- and fluorine-free siliceous oxyapatite.

3. Apatite glass ceramic according to claim 1, in which the one or more oxyapatite phases have the formula Me[I]Me[III]$_9$(SiO$_4$)$_6$O$_2$, Me[II]$_2$Me[III]$_8$(SiO$_4$)$_6$O$_2$ and/or Me[III]$_{9.33}$(SiO$_4$)$_6$O$_2$.

4. Apatite glass ceramic according to claim 1, in which Me[I], Me[II] and Me[III] are metal cations and Me[I] is Na or Li, Me[II] Ca or Sr and Me[III] Y or La.

5. Apatite glass ceramic according to claim 3, in which the one or more oxyapatite phases have the formula NaY$_9$(SiO$_4$)$_6$O$_2$, LiY$_9$(SiO$_4$)$_6$O$_2$, Sr$_2$Y$_8$(SiO$_4$)$_6$O$_2$, Ca$_2$Y$_8$(SiO$_4$)$_6$O$_2$, Sr$_2$La$_8$(SiO$_4$)$_6$O$_2$ and/or La$_{9.33}$(SiO$_4$)$_6$O$_2$.

6. Apatite glass ceramic according to claim 1, further comprising at least one further crystalline phase.

7. Apatite glass ceramic according to claim 6, which contains leucite as a further crystalline phase.

8. Apatite glass ceramic according to claim 1, which contains the following components, the percentages relating to the total mass of the glass ceramic:

| | |
|---|---|
| $SiO_2$ | 40 to 70 wt.-% |
| $B_2O_3$ | 0 to 9 wt.-% |
| $Al_2O_3$ | 7 to 15 wt.-% |
| $Y_2O_3$ | 0 to 14 wt.-% |
| $La_2O_3$ | 0 to 17 wt.-% |
| $ZrO_2$ | 0 to 3 wt.-% |
| $LiO_2$ | 0 to 8 wt.-% |
| $Na_2O$ | 0 to 24 wt.-% |
| $K_2O$ | 0 to 14 wt.-% |
| CaO | 0 to 9 wt.-% |
| SrO | 0 to 15 wt.-% |
| F | 0 to 3 wt.-%. |

9. Apatite glass ceramic according to claim 8 which contains the following components:

| | |
|---|---|
| $SiO_2$ | 45.9 to 64.0 wt.-% |
| $B_2O_3$ | 0 to 8.5 wt.-% |
| $Al_2O_3$ | 7.9 to 14.3 wt.-% |
| $Y_2O_3$ | 0 to 12.0 wt.-% |
| $La_2O_3$ | 0 to 14.9 wt.-% |
| $ZrO_2$ | 0 to 1.7 wt.-% |
| $LiO_2$ | 0 to 6.0 wt.-% |
| $Na_2O$ | 0 to 20.0 wt.-% |
| $K_2O$ | 0 to 11.6 wt.-% |
| CaO | 0 to 7.3 wt.-% |
| SrO | 0 to 12.8 wt.-% |
| F | 0 to 2.2 wt.-%. |

10. Apatite glass ceramic according to claim 8 which contains one or more chromophoric or fluorophoric metal oxides.

11. Apatite glass ceramic according to claim 10 in which the metal of the metal oxide or the metals of the metal oxides are selected from the group of the 3d and 4f elements of the periodic table of the elements.

12. Apatite glass ceramic according to claim 1 in which the proportion of apatite crystals is at least 5 wt.-%.

13. Apatite glass ceramic according to claim 1 in which the apatite crystals are needle-shaped.

14. Apatite glass ceramic according to claim 1 in which the apatite crystals have an average length of 0.1 to 10 μm.

15. Apatite glass ceramic according to claim 1 which in the temperature range of 100 to 500° C. the apatite glass ceramic has a coefficient of thermal expansion of $6*10^{-6} K^{-1}$ to $15*10^{-6} K^{-1}$.

16. Apatite glass ceramic according to claim 1 which has a firing temperature of 830° C. to 1150° C.

17. Apatite glass ceramic according to claim 1 which has a chemical resistance of <80 μg/cm².

18. Method for the production of an apatite glass ceramic according to claim 1, in which (a) starting components required for the production of the glass ceramic are mixed and are melted to form a glass,
(b) the glass melt from step (a) is transformed into a glass granulate,
(c) the glass granulate is optionally ground to a powder with an average grain size of 1 to 500 μm, and
(d) the glass granulate from step (b) or the glass powder from step (c) is then subjected to a single- or multi-stage thermal treatment in the temperature range of 700 to 1200° C. for a period of 30 minutes to 6 hours.

19. Method according to claim 18 in which the glass granulate from step (b) or the glass powder from step (c) is subjected to a thermal treatment in the temperature range of 900 to 1200° C. in step (d).

20. Method according to claim 18 in which the glass granulate from step (b) or the glass powder from step (c) is subjected to a thermal treatment for a period of 30 minutes to 3 hours in step (d).

21. Multi-component material which contains, as first component, at least one apatite glass ceramic according to claim 1 in powder form and, as second component, contains at least one further glass and/or glass ceramic powder.

22. Material according to claim 21 which contains, as second component, an alkali-zinc-silicate glass which contains the following components:

| | |
|---|---|
| $SiO_2$ | 52.0 to 63.5 wt.-% |
| $Me'[III]_2O_3$ | 8.5 to 13.0 wt.-% |
| $K_2O$ | 0 to 20.5 wt.-% |
| $Na_2O$ | 1.5 to 20.0 wt.-% |
| $LiO_2$ | 0 to 5.0 wt.-% |
| ZnO | 3.6 to 8.0 wt.-% |
| Me'[II]O | 2.5 to 6.5 wt.-% |
| $TiO_2 + ZrO_2$ | 0.5 to 6.0 wt.-% |
| $SnO_2$ | 0 to 9.5 wt.-% |
| $P_2O_5$ | 0 to 4.0 wt.-% |
| F | 0 to 2.0 wt.-% |
| $CeO_2$ | 0 to 3.0 wt.-%, | where
(a) Me'[III]$_2$O$_3$ is formed by 0 to 13 wt.-% $Al_2O_3$ and 0 to 9.5 wt.-% $La_2O_3$ and
(b) Me'[II]O is formed by 0 to 3.5 wt.-% CaO, 0 to 4.5 wt.-% BaO and 0 to 5.0 wt.-% MgO.

23. Mixed glass ceramic which can be obtained by mixing the components of a material according to claim 21 and then transforming them into a mixed glass ceramic.

24. A method comprising forming a dental substructure and applying an opacifying component comprised of an apatite glass ceramic according to claim 1 to the dental substructure to produce a dental material or dental restoration.

25. The method according to claim 24, wherein the dental material is a coating material or facing material.

26. The method according to claim 24, wherein the dental restoration is a crown, bridge, partial crown, an onlay, an artificial tooth, a stump superstructure or a facet.

* * * * *

UNITED STATES PATENT AND TRADEMARK OFFICE
CERTIFICATE OF CORRECTION

PATENT NO. : 7,166,548 B2 Page 1 of 1
APPLICATION NO. : 10/973233
DATED : January 23, 2007
INVENTOR(S) : Apel et al.

It is certified that error appears in the above-identified patent and that said Letters Patent is hereby corrected as shown below:

Cover page at (75) Inventors: "Christian van't Hoen, Feldkirch (AT)" should be --Christian Ritzberger, Feldkirch (AT)--.

Signed and Sealed this

Third Day of April, 2007

JON W. DUDAS
*Director of the United States Patent and Trademark Office*